US012766435B2

(12) United States Patent
Sheehan et al.

(10) Patent No.: US 12,766,435 B2
(45) Date of Patent: Oct. 20, 2026

(54) NUCLEATION OF LARGE-SCALE PROTEIN CRYSTALS FROM NANOPARTICLE SEEDS

(71) Applicant: Khalifa University of Science and Technology, Abu Dhabi (AE)

(72) Inventors: David Sheehan, Abu Dhabi (AE); Syed Salma Sultana, Abu Dhabi (AE); Praveen Managutti, Abu Dhabi (AE)

(73) Assignee: Khalifa University of Science and Technology, Abu Dhabi (AE)

( * ) Notice: Subject to any disclaimer, the term of this patent is extended or adjusted under 35 U.S.C. 154(b) by 455 days.

(21) Appl. No.: 18/368,212

(22) Filed: Sep. 14, 2023

(65) Prior Publication Data

US 2025/0099871 A1 Mar. 27, 2025

(51) Int. Cl.
*B01D 9/00* (2006.01)
*C07K 1/30* (2006.01)

(52) U.S. Cl.
CPC ........... *B01D 9/005* (2013.01); *B01D 9/0077* (2013.01); *C07K 1/306* (2013.01); *B01D 2009/0086* (2013.01)

(58) Field of Classification Search
CPC .................. B01D 9/005; B01D 9/0077; B01D 2009/0086; C07K 1/306; C30B 29/58; C30B 7/00
See application file for complete search history.

(56) References Cited

U.S. PATENT DOCUMENTS

2022/0099675 A1 * 3/2022 Chen ................ G01N 33/56983

FOREIGN PATENT DOCUMENTS

WO WO-2011013857 A1 * 2/2011 ............. C07K 1/306

OTHER PUBLICATIONS

Rubin et al. "Minimal intervention robotic protein crystallization" Journal of Crystal Growth vol. 110 1991 pp. 156-163.*

Molecular Dimensions Molecular Dimensions Monograph Series 2007.*

Emadiasum.com "Photoetched Cover slips Round" from Lin et al 1981.*

Burley, Stephen K., et al., "RCSB Protein Data Bank: powerful new tools for exploring 3D structures of biological macromolecules for basic and applied research and education in fundamental biology, biomedicine, biotechnology, bioengineering and energy sciences", Nucleic Acids Research, 2021, vol. 49, Database issue D437-D451.

Dahms, Sven O., et al., "Structure of the unliganded form of the proprotein convertase furin suggests activation by a substrate-induced mechanism", Proceedings of the National Academy of Sciences of the United States of America , vol. 113, No. 40 (Oct. 4, 2016), pp. 11196-11201.

Devi, Kasi Pandima, et al., "A perspective on the applications of furin inhibitors for the treatment of SARS-CoV-2", Pharmacological Reports (2022) 74:425-430.

* cited by examiner

*Primary Examiner* — Robert M Kunemund
(74) *Attorney, Agent, or Firm* — Billion & Armitage

(57) ABSTRACT

Embodiments of the present disclosure describe an ultra-high condition prescreening protein crystallization kit, comprising: (a) gold nanoparticles coated with PEG (polyethylene glycol); (b) ultra-high conditions scaled up to screen; (c) a plurality of cover slips with a recess; (d) a plurality of greased Linbro plates. Embodiments of the present disclosure also describe a modified hanging drop method for protein crystallization.

20 Claims, 12 Drawing Sheets

BSA protein
(globular structure)

○ No Growth ● Growth

| S.NO | Protein condition | Units | Salt | Nanoparticles + PEG 4000 | Percentage |
|---|---|---|---|---|---|
| A | 20 | 0.4M | Ammonium formate | AuNP + Polyethylene glycol 4000 | 6% v/v |
| B | 40 | 0.8M | Potassium thiocyanate | AuNP + Polyethylene glycol 4000 | 10% v/v |
| C | 74 | 0.4M | DL-Malic acid pH 7.1 | AuNP + Polyethylene glycol 4000 | 6% v/v |
| D | 101 | 0.8M | Ethylammonium nitrate | AuNP + Polyethylene glycol 4000 | 10% v/v |
| E | 105 | 0.4M | Magnesium nitrate hexahydrate | AuNP + Polyethylene glycol 4000 | 6% v/v |
| F | 202 | 0.6M | Potassium citrate tribasic monohydrate | AuNP + Polyethylene glycol 4000 | 8% v/v |

FIG. 7A

| CRYSTAL UNIT CELL DIMENSION | A 250 NM - SIZE | B 300 NM – SIZE | C 400 NM -SIZE |
|---|---|---|---|
| a (Å) | 27.31 (14) | 46.3 (10) | 50.18 (7) |
| b (Å) | 13.04 (12) | 65.3 (4) | 67.7 (2) |
| c (Å) | 68.4 (7) | 98.5 (4) | 68.0 (2) |
| α (Å) | 89 (1) | 89.8 (4) | 92.4 (4) |
| ß (Å) | 93..9 (7) | 98 (1) | 110.7 (2) |
| Y (Å) | 89.8 (6) | 110 (1) | 100.6 (3) |

FIG. 7B

NUCLEATION OF LARGE-SCALE PROTEIN CRYSTALS FROM NANOPARTICLE SEEDS

BACKGROUND

Proteins are the most important biological macromolecules and are involved in almost all aspects of life. Therefore, the study of the structure of proteins is of great practical and fundamental importance. On the one hand, knowledge of the spatial structure of proteins is necessary to study the basic principles of protein functioning; for example, the mechanisms of enzymatic reactions. On the other hand, knowledge of the spatial structure of proteins is used, for example, in biotechnology, for the design of enzymes with desired properties, as well as in drug design. The traditional method for determining the spatial structure of a protein is X-ray structural analysis of protein crystals. The main difficulty in applying this method is in obtaining a perfect protein-crystal. Protein crystallization has its own set of challenges because it depends on a number of factors.

SUMMARY

In general, embodiments of the present disclosure describe an ultra-high condition prescreening protein crystallization kit and a modified method for protein crystallization.

Accordingly, embodiments of the present disclosure describe an ultra-high condition prescreening protein crystallization kit comprising gold nanoparticles coated with PEG (polyethylene glycol), ultra-high conditions scaled up to screen, a plurality of coverslips with a recess and a plurality of greased Linbro plates; wherein the kit uses a modified hanging drop method for carrying out the protein crystallization.

Embodiments of the present disclosure describe a modified hanging drop method for protein crystallization comprising creating a recess on a coverslip, pouring a target protein solution and a precipitant solution in the recess on the coverslip sufficient to form a drop; wherein the precipitant solution comprises gold nanoparticles. This is followed by inverting the coverslip without disturbing the drop and placing the inverted coverslip onto a sealed well of a greased reservoir, wherein the rim of the reservoir is greased, and gently applying pressure on the silicon grease on the rim of the reservoir to create an airtight seal. The above steps are repeated with all the buffer combinations listed in the ultra-high conditions and then allowing the plate to rest undisturbed at a temperature of 18-22° C. to facilitate crystallization and visually inspecting the plate for crystallization.

BRIEF DESCRIPTION OF DRAWINGS

This written disclosure describes illustrative embodiments that are non-limiting and non-exhaustive. Reference is made to illustrative embodiments that are depicted in the figures, in which:

FIG. 7A shows the table for the protein conditions, buffers and nanoparticles used in the Furin experimental data of FIGS. 6(A)-6(G). FIG. 7B provides the crystal data of unit cell volume for Furin.

DETAILED DESCRIPTION

Figure 1:
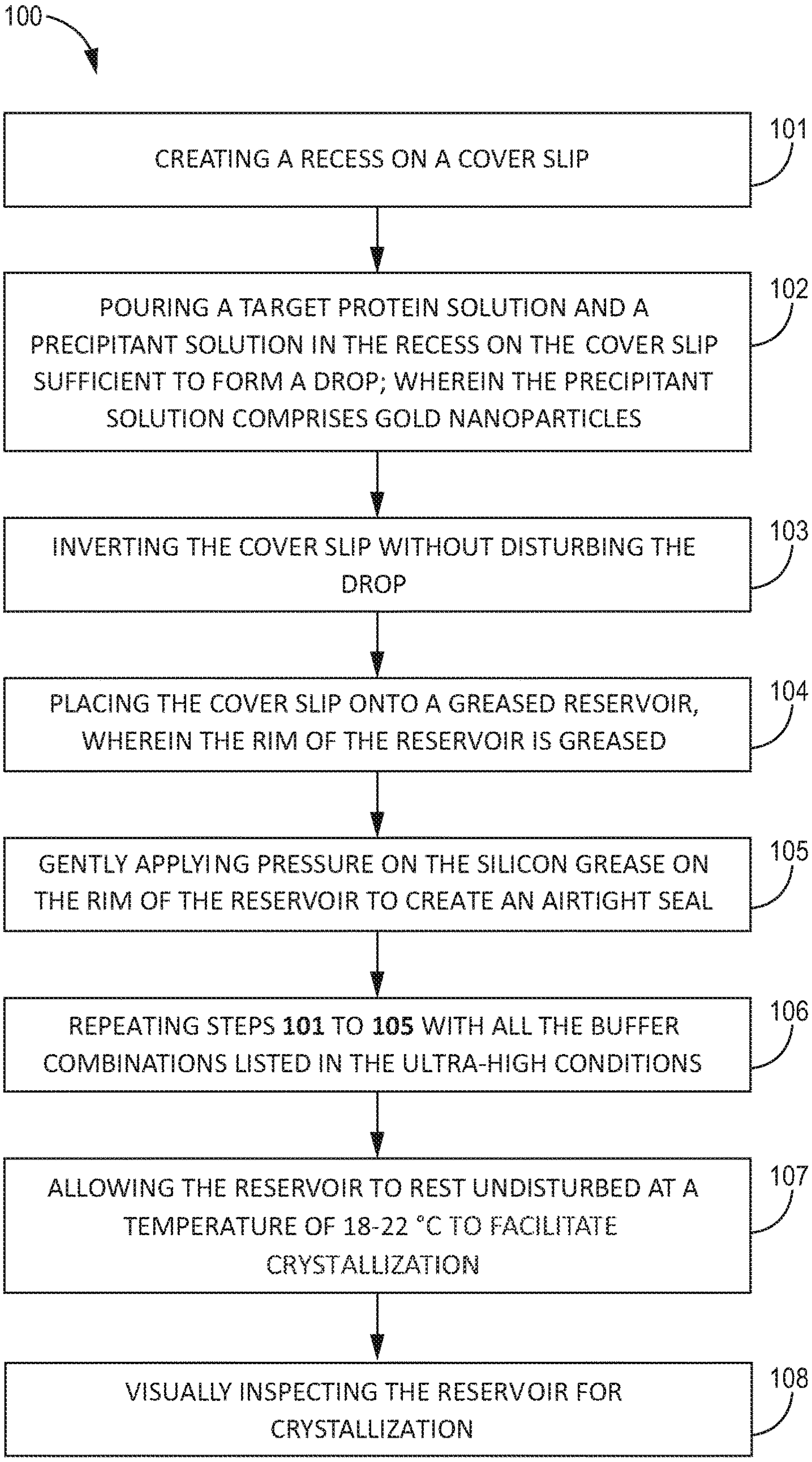
FIG. 1 illustrates a flowchart of a modified hanging drop method for protein crystallization, according to some embodiments.

The present disclosure relates to a method for the nucleation of large-scale proteins crystals from nanoparticles seeds. Particularly, this method illustrates protein crystallization without the use of ligands, His-tags, or other modifications. In fact, many proteins are crystallized in their native, unmodified state, which is very important for studying their natural structure and function of proteins. However, the crystallization process can be challenging, and often requires a great deal of optimization of the conditions to obtain high-quality crystals. Embodiments of the present disclosure describe a prescreening protein crystallization kit of ultra-high conditions of at least 200 conditions screen which has nanoparticle seeds with coated polymers, which are stable for about 3-5 years.

Embodiments of the present disclosure describe an ultra-high condition prescreening protein crystallization kit, comprising: (a) gold nanoparticles coated with PEG (polyethylene glycol); (b) ultra-high conditions scaled up to screen; (c) a plurality of cover slips with a recess; (d) a plurality of greased Linbro plates. Embodiments of the present disclosure describe a kit, which may further comprise instructions for carrying out the method of crystallization including troubleshooting tips. According to one or more embodiments of the present disclosure, the kit describes the method of crystallization as the modified hanging drop method. Some embodiments of the present disclosure describe a kit wherein the coverslip is a plastic coverslip. Certain other embodiments of the present disclosure describe a kit, wherein the gold nanoparticles are coated with PEG in different concentrations in buffer. Some embodiments of the present disclosure describe a kit, wherein the gold nanoparticles are monodispersed. Yet other embodiments of the present disclosure describe a kit, wherein the nanoparticles are stable at room temperature. One or more embodiments of the present disclosure describe a kit, wherein the nanoparticles have a shelf life of 3-5 years. Yet other embodiments of the present disclosure describe a kit, wherein the nanoparticles have a shelf life of 3 years. Some embodiments of the present disclosure describe a kit, wherein the ultra-high condition may comprise at least 200 conditions scaled up to screen. Yet other embodiments of the present disclosure describe a kit, wherein the ultra-high condition may comprise at least 150 conditions scaled up to screen. One or more embodiments of the present disclosure describe a kit, wherein the ultra-high condition may comprise at least 96 conditions scaled up to screen.

Embodiments of the present disclosure describe a modified hanging drop method for protein crystallization. The method comprises creating a recess on a cover slip. The recess may be in the form of a shallow well. This is followed by pouring a target protein solution and a precipitant solution in the recess on the coverslip sufficient to form a drop. The coverslip is then inverted without disturbing the drop. This is followed by placing the coverslip onto a sealed well of a greased reservoir and gently applying pressure or tapping on the silicon grease on the rim of the reservoir to create an airtight seal. The reservoir may include, but is not limited to, a Linbro plate, cuvette(s). The above steps are repeated with all the buffer combinations listed in the ultra-high conditions. The reservoir or Linbro plate is then placed in a quiet area (away from extreme vibrations, temperature fluctuations, and pedestrian traffic) once the matrix is complete. The reservoir(s) or plate is allowed to rest undisturbed at room temperature or at a temperature of 18-22° C. to facilitate crystallization. The plate is visually inspected for crystallization. The visual inspection may include, but is not limited to, inspecting under a standard laboratory microscope. This is done by inverting the reservoir or Linbro plate on the stage of a standard laboratory microscope ensuring that the coverslip is in focus.

FIG. 1 is a flowchart of a modified hanging drop method for protein crystallization, according to one or more embodiments of the present disclosure. As shown in FIG. 1, the method may comprise creating 101 a recess on a coverslip and pouring 102 a target protein solution and a precipitant solution in the recess on the coverslip sufficient to form a drop. This is followed by inverting 103 the coverslip without disturbing the drop and placing 104 the inverted coverslip onto a greased reservoir, wherein the rim of the reservoir is greased. This is followed by gently applying 105 pressure on the silicon grease on the rim of the reservoir to create an airtight seal. Repeating 106 the steps 101 to 105 with all the buffer combinations listed in the Ultra high conditions. Allowing 107 the reservoir to rest undisturbed at a temperature of to facilitate crystallization and visually inspecting 108 the reservoir for crystallization.

Step 101 includes creating a recess on a coverslip. The coverslip may comprise a plastic coverslip. The coverslip may be silanated. The recess may be in the form of a shallow well. The recess or shallow well on the coverslip has the capacity of volume in the range of 0.5 μl-10 μl. The recess or shallow well on the coverslip may have the capacity of volume in the range of 0.2 μl-20 μl.

Step 102 includes pouring a target protein solution and a precipitant solution in the recess on the coverslip sufficient to form a drop. The target protein solution comprises the protein to be crystallized and wherein the target protein is in a buffer solution. The target protein solution comprises the target protein in a concentration of 5 mg/ml to 40 mg/ml.

The precipitant solution comprises the coated gold nanoparticles in a buffer and wherein the gold nanoparticles are coated with capping agents. The capping agents include, but are not limited to, one or more of PEG, PVP, BSA, CIT. The buffer comprises one or more of the buffers given in the ultra-high conditions. The buffers contain different concentrations of the salts given in the ultra-high conditions. The gold nanoparticles are monodispersed, and the size of the gold nanoparticles can be tuned. The protein crystallization is induced by the gold nanoparticles and the nanoparticles induced protein crystallization may depend on the size of the nanoparticles. The gold nanoparticles may comprise, but is not limited to, an average diameter in the range of 3.2 to 5.2 nm. The gold nanoparticles may comprise, but is not limited to, an average diameter in the range of 3-6 nm. The gold nanoparticles may comprise, but is not limited to, an average diameter in the range of 2.5-10 nm. The gold nanoparticles may comprise, but is not limited to, an average diameter in the range of 5-25 nm. The gold nanoparticles may comprise, but is not limited to, an average diameter in the range of 10-20 nm. The gold nanoparticles are stable at room temperature. The gold nanoparticles may have a shelf life of 3-5 years. The gold nanoparticles may have a shelf life of 3 years.

Step 103 includes inverting the coverslip without disturbing the drop. For the drop to be not disturbed, the drop should remain unperturbed even while inverting the coverslip.

Step 104 includes placing the inverted coverslip onto a greased reservoir. For example, if a Linbro plate is used, the rim of the Linbro plate is greased. The reservoir may include, but is not limited to, a cuvette or a Linbro plate. The reservoir may have a capacity of volume in the range of 1 ml to 5 ml. The reservoir may have a capacity of volume in the range of 0.5 ml to 3 ml.

Step 105 includes gently applying pressure on the silicon grease on the rim of the reservoir to create an airtight seal. Pressure may be applied by tapping on the rim of the reservoir or Linbro plate.

Step 106 includes repeating the steps 101 to 105 with all the buffer combinations listed in the ultra-high conditions. The ultra-high conditions include a list of different buffer combinations along with the capped AuNP and the percent of PEG used for capping. The ultra-high condition may comprise at least 200 conditions scaled up to screen. The ultra-high condition may comprise at least 150 conditions scaled up to screen. The ultra-high condition may comprise at least 96 conditions scaled up to screen.

Step 107 includes allowing the reservoir to rest undisturbed at a temperature of 18-22° C. to facilitate crystallization. The temperature at which crystallization may take place may vary. The temperature at which crystallization may take place may be room temperature. The temperature at which crystallization may take place may be in the range of 15-30° C. The temperature at which crystallization may take place may be in the range of 22-37° C. The duration at which crystallization may occur may vary. The duration of crystallization ranges from 2 hours to 245 hours. The duration of crystallization may range from 4 hours to 210 hours. In some embodiments of the present disclosure, the duration of crystallization may range from 3 hours to 14 hours.

Step 108 includes visually inspecting the reservoir for crystallization. Visual inspection may comprise using a range of equipment. Visual inspection may comprise, but is not limited to, using a standard laboratory microscope. For the visual inspection using standard laboratory microscope, the inspection is made by inverting the reservoir or plate on the stage of a standard laboratory microscope ensuring that the coverslip is in focus.

Embodiments of the present disclosure describe a method, wherein the capping agents comprise one or more of PEG, PVP, BSA, CIT. Some embodiments of the present disclosure describe a method, wherein the buffer comprises one or more of the buffers given in the ultra-high conditions. Some embodiments of the present disclosure describe a method, wherein the ultra-high condition may comprise at least 200 conditions scaled up to screen. Yet other embodiments of the present disclosure describe a method, wherein the ultra-high conditions may comprise at least 150 conditions scaled up to screen. Certain other embodiments of the present disclosure describe a method, wherein the ultra-high conditions may comprise at least 96 conditions scaled up to screen. TABLE 4 shows the ultra-high conditions of at least 200 conditions for prescreening of protein crystallization.

Some embodiments of the present disclosure describe a method, wherein the coverslip is a plastic coverslip and is silanated. Some embodiments of the present disclosure describe a method, wherein the coverslip has a recess or shallow well. Some embodiments of the present disclosure describe a method, wherein the recess or shallow well on the coverslip has the capacity of volume in the range of 0.5 μl-10 μl. Yet other embodiments of the present disclosure describe a method, wherein the recess or shallow well of the coverslip may have the capacity of volume in the range of 0.2 μl-20 μl.

Embodiments of the present disclosure describe a method, wherein the target protein solution comprises the protein to be crystallized and wherein the target protein is in a buffer solution. Embodiments of the present disclosure describe a method, wherein the target protein solution comprises APO proteins. Some embodiments of the present disclosure describe a method, wherein the target protein solution comprises the target protein in a concentration of 5 mg/ml to 40 mg/ml. Some embodiments of the present disclosure describe a method, wherein the target protein solution comprises the target protein in a concentration of 9 mg/ml to 20 mg/ml.

Embodiments of the present disclosure describe a method, wherein the precipitant solution comprises the coated gold nanoparticles in a buffer and wherein the gold nanoparticles are coated with capping agents. Some embodiments of the present disclosure describe a method, wherein the capping agents comprise, but is not limited to, one or more of PEG (polyethylene glycol), PVP (polyvinyl pyrrolidone), BSA (Bovine Serum Albumin), CIT (Citric acid). One or more embodiments of the present disclosure describe a method, wherein the gold nanoparticles are monodispersed. One or more embodiments of the present disclosure describe a method, wherein the size of the gold nanoparticles can be tuned. Yet other embodiments of the present disclosure describe a method, wherein the protein crystallization is nanoparticle induced and wherein the nanoparticle induced protein crystallization may depend on the size of the nanoparticles and wherein the average diameter of gold nanoparticles was precisely controlled from 3.2 to 5.2 nm. Some embodiments of the present disclosure describe a method wherein the average diameter of gold nanoparticles is in the range of 2.0 to 52.0 nm. Some embodiments of the present disclosure describe a method wherein the average diameter of gold nanoparticles is in the range of 3-6 nm. Some embodiments of the present disclosure describe a method wherein the average diameter of gold nanoparticles is in the range of 2.5-10 nm. Some embodiments of the present disclosure describe a method wherein the average diameter of gold nanoparticles is in the range of 5-25 nm. Some embodiments of the present disclosure describe a method wherein the average diameter of gold nanoparticles is in the range of 10-20 nm. One or more embodiments of the present disclosure describe a method wherein the buffer, the target protein solution and the precipitant solution are in the ratio of 3:2:1.

Embodiments of the present disclosure describe a method, wherein the buffer comprises one or more of the buffers given in the ultra-high conditions. One or more embodiments of the present disclosure describe a method, wherein the buffer comprises one or more of the buffers given in the at least 200 conditions and wherein the buffers contain different concentrations of the salts given in the at least 200 conditions.

Embodiments of the present disclosure describe a method, wherein the duration of crystallization ranges from a few hours to a few days. Yet other embodiments of the present disclosure describe a method, wherein the duration of crystallization ranges from 2 hours to 245 hours. Some embodiments of the present disclosure describe a method, wherein the duration of crystallization ranges from 4 hours to 210 hours. One or more embodiments of the present disclosure describe a method, wherein the duration of crystallization ranges from 3 hours to 14 hours. TABLE 1 shows target proteins and their crystallization time/duration of crystallization.

TABLE 1

TARGET PROTEINS AND THEIR DURATION OF CRYSTALLIZATION

| S/NO | PROTEINS | SCREENING | HOURS |
|---|---|---|---|
| 1 | Alginate lyase 7A 1 mg, NZYTeck | ++ | 12 |
| 2 | Lysozyme 23A 1 mg, NZYTech | ++ | 6 |
| 3 | Oligogalacturonate lyase 22A 1 mg, NZYTech | ++ | 16 |
| 4 | Arabinoxylanase 5A 1 mg, NZYTech | ++ | 10 |
| 5 | Native Microorganism Glycerol Kinase: 30 U/mg; 20 KU | ++ | 4 |
| 6 | Native *Escherichia coli* β-Galactosidase: ≥300 units per mg protein: 1 KU Creative-Enzymes | ++ | 7 |
| 7 | Native Porcine L-Lactate Dehydrogenase: 550 U/mg protein, 25 KU. | ++ | 96 |
| 8 | Native Porcine α-Amylase: 100 U/mg protein, 25 KU | ++ | 210 |
| 9 | Fructosyl-Amino Acid Oxidase from *E. coli*, Recombinant: 100 U/mg protein; 10 mg | | |
| 10 | Native Porcine L-Lactate Dehydrogenase: 550 U/mg protein, 25 KU. | ++ | 101 |
| 11 | Sarcosine Oxidase from *E. coli*, Recombinant: >10 U/mg; 50 KU | ++ | 56 |
| 12 | Native *Pseudomonas* sp. Formaldehyde Dehydrogenase: 1-6 U/mg; 5 U | ++ | 84 |
| 13 | Native *Pseudomonas* sp. Lipoprotein lipase: ≥20 U/mg 5 KU 1 | ++ | 72 |
| 14 | Native *Bacillus* sp. Leucine dehydrogenase, 20 U/mg: 1 KU 1 ea. | ++ | 24 |
| 15 | Furin from Human, Recombinant: >125 pmol/min/μg, 10 ug | ++ | 18 |

Embodiments of the present disclosure describe a method, wherein the nanoparticles are stable at room temperature. Certain embodiments of the present disclosure describe a method, wherein the nanoparticles have a shelf life of 3-5 years. One or more embodiments of the present disclosure describe a method, wherein the nanoparticles have a shelf life of 3 years.

EXAMPLES

Example 1: Synthesis of Gold Nanoparticles

A 50 mM stock solution of $AuCl_4^-$ was made by dissolving $HAuCl_4$ 33$H_2O$ with an equimolar amount of HCl in a glass vial, ensuring stability for several months. In a separate glass beaker, a 50 mM stock solution of $BH_4^-$ was made by dissolving $NaBH_4$ granules with an equimolar amount of NaOH, stable for a few hours at room temperature. For 3.2 nm nanoparticles, 100 μL of $AuCl_4^-/H^+$ solution was added to water in a vial, followed by swift injection of 300 μL of $BH_4^-/OH^-$ solution. Stirring for 1 minute led to an immediate color change from yellow to red, accompanied by the release of hydrogen gas molecules. Overall, the method successfully produced small red nanoparticles, with a smooth and efficient reaction.

For nanoparticles of other sizes, the amount of the $BH_4^-/OH^-$ solution was increased from 300 to 650 μL followed by heating for 1-2 min at the boiling temperature of water on a hot plate. The average diameter of gold nanoparticles was precisely controlled from 3.2 to 5.2 nm. The amount of the $BH4^-/OH^-$ solution was changed from 300 to 1400 μL during the search for the "PRIME ZONE" before heating. PRIME ZONE is the region where fast growth of crystal nuclei occurs. In other words, Prime Zone refers to the optimum condition for crystal nuclei formation. Stabilizer-Free Gold Nanoparticles in Water: Neutral gold atoms reduced from gold ions in water meet each other and form nanoparticles that are stable via electrostatic repulsion due to adsorbed anions. In nanoparticle synthesis, it is challenging to simultaneously tune the size and guarantee a monodisperse size distribution. Gold nanoparticles made by using citric acid as both a weak (slow reaction for 30-60 min while boiling the solution) reducer and a stabilizer; and refined by Frens 25 at a diameter range of 20-40 nm, which is far too large for phase-transfer to nonpolar solvents. Nanoparticles of various sizes were produced by adjusting the amount of $BH_4^-/OH^-$ solution from 300 to 650 L, followed by heating for 2-3 minutes at the boiling temperature of water on a hot plate. This controlled the average diameter of the gold nanoparticles precisely, ranging from 3.2 to 5.2 nm. Before heating, the amount of $BH_4^-/OH^-$ solution was varied from 200 to 1300 μL during the search for an optimal synthesis condition. The goal was to achieve both desired nanoparticle size and a monodisperse size distribution. In this synthesis process, neutral gold atoms were reduced from gold ions in water and subsequently assembled into nanoparticles stabilized by electrostatic repulsion due to adsorbed anions. Citric acid was utilized as a weak reducer and stabilizer during the synthesis of gold nanoparticles. The reaction was slow, lasting 30-60 minutes while the solution was boiled. The nanoparticles were further refined using the Frens 25 method, resulting in a diameter range of 10-20 nm. However, these nanoparticles were too large for phase-transfer to nonpolar solvents.

For fast formation of gold nanoparticles at room temperature within a few seconds, strong reducers are used: alkaline tetrakis (hydroxymethyl) phosphonium chloride (THPC) 26 for diameters <2 nm and isoascorbic acid for the diameter of ~50 nm. Another strong reducer, borohydride can also generate gold nanoparticles within a few seconds, whose size varies from 2 nm to >50 nm with the solution's color varying among brown, orange, red, and purple. Solutions of borohydride freshly prepared and/or cooled down in an ice bath are used to slow down the reaction rate of borohydride with water molecules and therefore increase the reproducibility. The much smaller size of borohydride compared with other molecules might be thought to be responsible for poor stability of gold nanoparticles in water. Adding the same molar amount of NaOH to the aqueous solution of borohydride keeps the reducing solution's reactivity steady for more than several hours at room temperature, which is an important point for high reproducibility. Similarly, adding the same molar amount of HCl to the gold chloride stock solution ensures stability for several months. Gold nanoparticles can be rapidly formed at room temperature within seconds using strong reducers. For nanoparticles with diameters below 2 nm, alkaline tetrakis (hydroxymethyl) phosphonium chloride (THPC) 26 is used, while isoascorbic acid is employed for nanoparticles with a diameter of around 50 nm. Borohydride is another potent reducer that produces gold nanoparticles ranging from 2 nm to over 50 nm, displaying various colors like brown, orange, red, and purple. To ensure consistent results, borohydride solutions are prepared freshly or cooled in an ice bath to slow down the reaction rate with water molecules. This enhances reproducibility. Despite its smaller size, borohydride's stability in water is improved by adding the same molar amount of NaOH to the reducing solution, maintaining its reactivity for several hours at room temperature. Similarly, the stability of the gold chloride stock solution is prolonged for several months by adding the same molar amount of HCl.

Figure 2A:
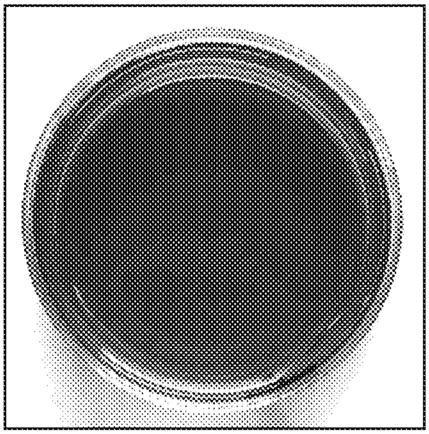
FIG. 2(*a*) and FIG. 2(*b*) show the real time images of the gold nanoparticles.
Figure 2B:
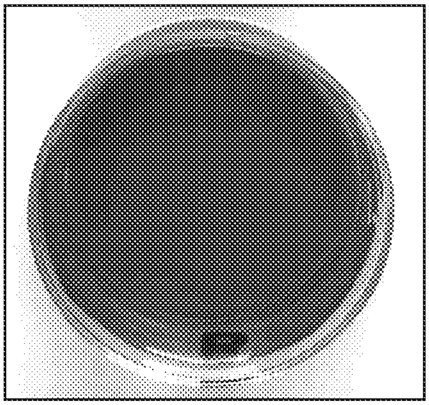

Since each borohydride anion has four reactive hydride arms and the gold ion's charge state is isotropic, three borohydride anions may reduce four gold ions to neutral gold atoms. However, the actual stoichiometry is not that simple due to the reactions of borohydride anions and gold chloride ions with protons and hydroxide anions, which were added to the two aqueous stock solutions for stability and reproducibility. In addition, excess boron-based anions are required as stabilizing anions for gold nanoparticles. Experimentally, it was discovered that there is a "Prime Zone" to obtain nearly monodisperse gold nanoparticles using only borohydride for reducing gold ions and stabilizing nanoparticles. The ratio of $BH_4^-/OH^-$ ions to $AuCl_4^-/H^+$ ions was adjusted carefully to make nearly monodisperse gold nanoparticles in water as shown in FIG. 2(*a*). Below the low boundary of 300% and above the high boundary of 1200%, the UV-vis spectra of gold nanoparticles in water have significant extinction around 700 nm, which indicates the existence of large gold nanoparticles, and therefore the size distribution is polydisperse. Each borohydride anion possesses four reactive hydride arms, potentially reducing four gold ions into neutral gold atoms due to the isotropic charge state of gold ions. However, the actual stoichiometry is more complex due to interactions with protons and hydroxide anions from the added stabilizers, ensuring stability and reproducibility. Excess boron-based anions serve as stabilizers for gold nanoparticles. The ratio of $BH_4^-/OH^-$ ions to $AuCl_4^-/H^+$ ions was adjusted to achieve nearly monodisperse gold nanoparticles. Outside the range of 300% to 1300%, the UV-vis spectra of gold nanoparticles in water indicated the presence of large gold nanoparticles and a polydisperse size distribution. Thus, precise control of the $BH_4^-/OH^-$ to $AuCl_4^-/H^+$ ratio is crucial for obtaining nearly monodisperse gold nanoparticles in water.

Within the "Prime Zone", between 300 and 1300%, extinction below ~450 nm and above ~600 nm is almost identical indicating that nearly monodisperse gold nanoparticles are made. If the extinction at ~400 nm is verified to be linearly proportional to the concentration of gold atoms, it can be used to normalize the UV-vis spectra for solutions with different concentrations of gold atoms. No software data normalization was performed; instead, the concentration of gold ions was fixed to 0.50 mM during the synthesis. Gold nanoparticles in water, without any stabilizing chemicals, are stabilized by physiosorbed boron-based anions, whose electrostatic repulsion energy decreases as the concentration of the screening ions increases. Screening ions are additional ions present in the surrounding solution, and they can be either positively charged (cations) or negatively charged (anions). Screening ions affect the electrostatic interactions between the boron-based anions and the gold nanoparticles by shielding the electrostatic forces. This partially explains why the size of nanoparticles and the plasmon peak around ~510 nm become larger with more $BH_4^-/OH^-$ ions in the "Prime Zone". It is suspected that the "prime zone" may be different at other concentrations of gold ions. As a strong reducing chemical, borohydride can reduce all gold ions to neutral gold atoms in less than 1 s at room temperature. The immediate color change from light yellow to orange indicates that all the gold ions are reduced to neutral gold atoms virtually simultaneously (fast nucleation). Small gold nanoparticles grow into larger ones by sintering (slow growth), changing the solution's color to red. Very quick reduction of all the gold ions may be responsible for the nearly monodisperse size distribution. Since gold nanoparticles initially grew rapidly and hydrogen gas bubbles changed light extinction significantly, the glass vial was kept shaking for 1 min to reach the slow growth stage and release hydrogen molecules. This 1 min step significantly increased the reproducibility of the UV-vis spectra and therefore the size of nanoparticles. One-minute shaking while exposed to aerial oxygen molecules might be important for oxidation of borohydride anions catalyzed by small gold nanoparticles which slows down as gold nanoparticles become larger than 3 nm in diameter. The discovery of the "Prime Zone" and the stabilization of stock solutions with HCl and NaOH are both very important for reproducibility and optimizing the synthesis parameters. The stabilizer-free gold nanoparticles in water produced by this method are stable for more than 1 year. Each borohydride anion possesses four reactive hydride arms, potentially reducing four gold ions into neutral gold atoms due to the isotropic charge state of gold ions. However, the actual stoichiometry is more complex due to interactions with protons and hydroxide anions from the added stabilizers, ensuring stability and reproducibility. Excess boron-based anions serve as stabilizers for gold nanoparticles. Researchers carefully adjusted the ratio of $BH_4^-/OH^-$ ions to $AuCl_4^-/H^+$ ions to achieve nearly monodisperse gold nanoparticles. Outside the range of 300% to 1300%, the UV-vis spectra of gold nanoparticles in water indicated the presence of large gold nanoparticles and a polydisperse size distribution. Thus, precise control of the $BH_4^-/OH^-$ to $AuCl_4^-/H^+$ ratio is crucial for obtaining nearly monodisperse gold nanoparticles in water.

Example 2: Polymer of Gold Nanoparticles Seeds

In order to endow the nanoparticles with electrosteric stability, the synthesized Gold nanoparticles were functionalized or coated with capping agents, which include, but is not limited to, PEG, PVP or BSA polymers by addition of an aqueous solution of the respective coating material (in concentration of 1% weight percentage of PEG, 4% Weight percentage PVP, and 0.6 mg $mL^{-1}$ BSA) to three separate beakers of the Gold nanoparticles dispersion in a 1:9 Volume ratio. After addition of the coating material, each mixture was stirred for one hour. The adsorption mechanism of each polymer is different, PEG molecules are covalently anchored to gold nanoparticles through their thiol terminal group. While for PVP, adsorption takes place through coordination with the N and O atoms in its heterocyclic ring. As for BSA, adsorption is believed to take place from multiple binding sites. BSA molecules can covalently adsorb onto gold nanoparticles via the thiol group from their cysteine residue. BSA can also absorb by electrostatic interactions that form salt bridges between its positive lysine residues and coating of gold nanoparticles. In order to have the same Au concentration in all four nanofluids, deionized water was added to the uncoated gold nanoparticles dispersion in the same 1:9 volume ratio. This ensured that the Au concentration in all four nanofluids was 0.1611 mg $mL^{-1}$ (used throughout this study, unless otherwise specified). This is equivalent to a gold volume fraction of 0.000417%. In order to rid of excess and residual material, all nanofluids were filtered using a stirred cell, through a 100 kDa membrane, and finally condensed to 50 mL each. This enabled to tune the size of the gold nanoparticles from 6-20 nm, extending the previous range of 3-6 nm. This in turn permits to explore size-dependent properties of nanoparticle-induced protein crystallization that were previously unexplored. Secondly, this method also helps quantify the acid/base stability of the gold nanoparticles thus synthesized, so as to fully explore a wider range of protein crystallization parameters. This method of synthesis of polymer of gold nanoparticle seeds provides with a clear vision of destabilization concentrations and can be directly applied to the crystallization conditions with any target protein. FIG. 3(*a*)-FIG. 3(*b*) shows the TEM of gold nanoparticles coated with PEG. TABLE 2 shows the capping agents and their structures.

Some embodiments of the present disclosure describe PEG was used as a capping agent for the synthesized gold nanoparticles to impart electrosteric stability. The functionalization process involved adding an aqueous solution of PEG to the gold nanoparticle dispersion at a concentration of 1% weight percentage. The mixture was stirred for one hour to ensure proper adsorption of PEG onto the gold nanoparticles. PEG molecules are covalently anchored to the gold nanoparticles through their thiol terminal group. Thiol Groups on PEG Molecules: PEG is a polymer composed of repeating ethylene glycol units. At one end of the PEG molecule, there is a thiol (—SH) functional group. This thiol group is highly reactive due to the sulfur atom, which has lone pairs of electrons that can form covalent bonds with other atoms or molecules. This process is typically referred to as PEGylation. To maintain the same gold concentration (0.1611 mg mL-1) in all nanofluids, deionized water was added in a 1:9 volume ratio to the uncoated gold nanoparticle dispersion. This step ensured that all nanofluids had the same Au concentration, equivalent to a gold volume fraction of 0.000417%. To obtain different PEG concentrations, the PEG solution was added at varying weight percentages, including 4%, 6%, 8%, 10%, 14%, and 16%. After functionalization, all nanofluids were filtered through a 100 kDa filter in a stirred cell to remove excess and residual materials. This in turn permits to explore size-dependent properties of nanoparticle-induced protein crystallization that were previously unexplored. Secondly, this method also helps quantify the acid/base stability of the gold nanoparticles thus synthesized, so as to fully explore a wider range of protein crystallization parameters. This method of synthesis of polymer of gold nanoparticle seeds provides with a clear vision of destabilization concentrations and can be directly applied to the crystallization conditions with any target protein.

Table 2: Capping Agents and their Structures

Figure 3A:
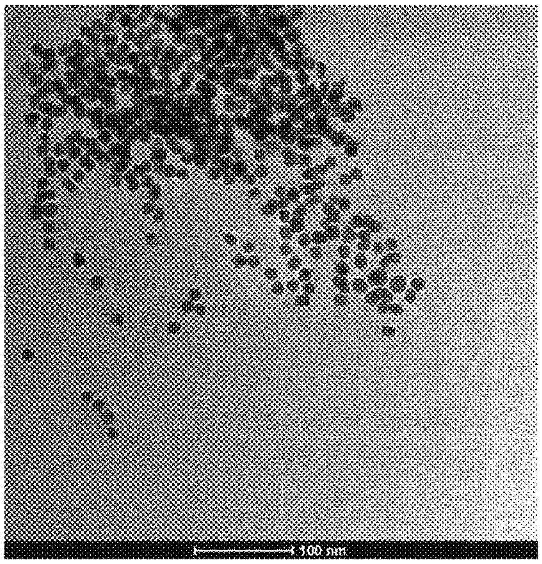
FIG. 3A-FIG. 3B show TEM of gold nanoparticles coated with PEG, according to some embodiments.
Figure 3B:
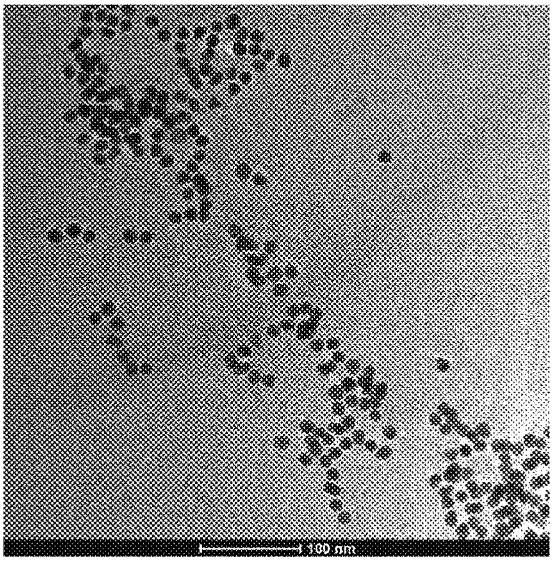
Figure 3C:
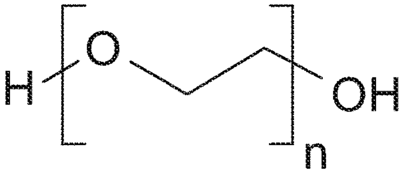
FIG. 3C illustrates the structure of PEG, according to some embodiments.
Figure 3E:
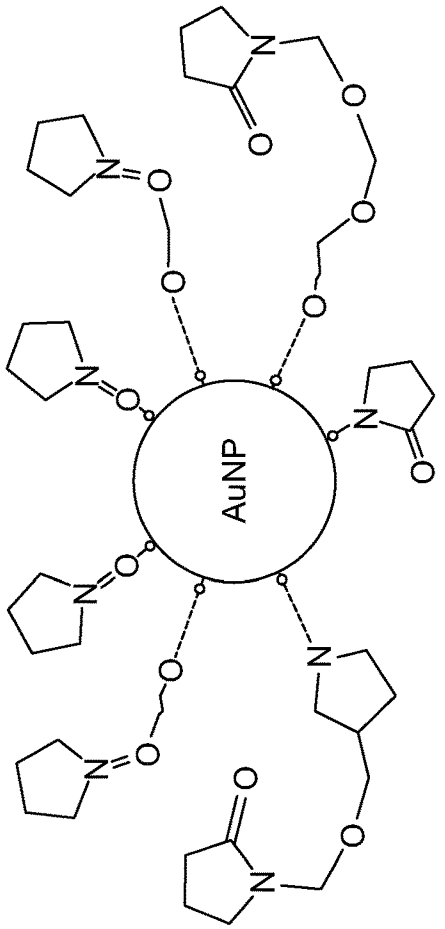
FIG. 3E illustrates coated gold nanoparticles using polyvinylpyrrolidone, according to some embodiments.
Figure 3D:
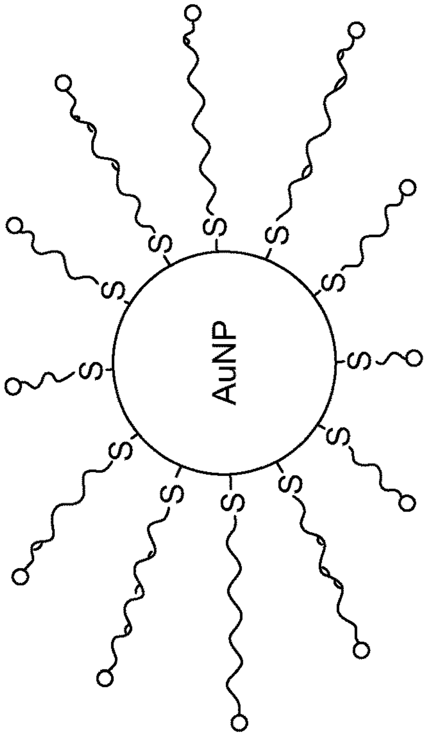
FIG. 3D illustrates coated gold nanoparticles using thiol-terminated PEG, according to some embodiments.
Figure 3F:
FIG. 3F illustrates a globular structure for BSA protein, according to some embodiments.
Figure 3G:
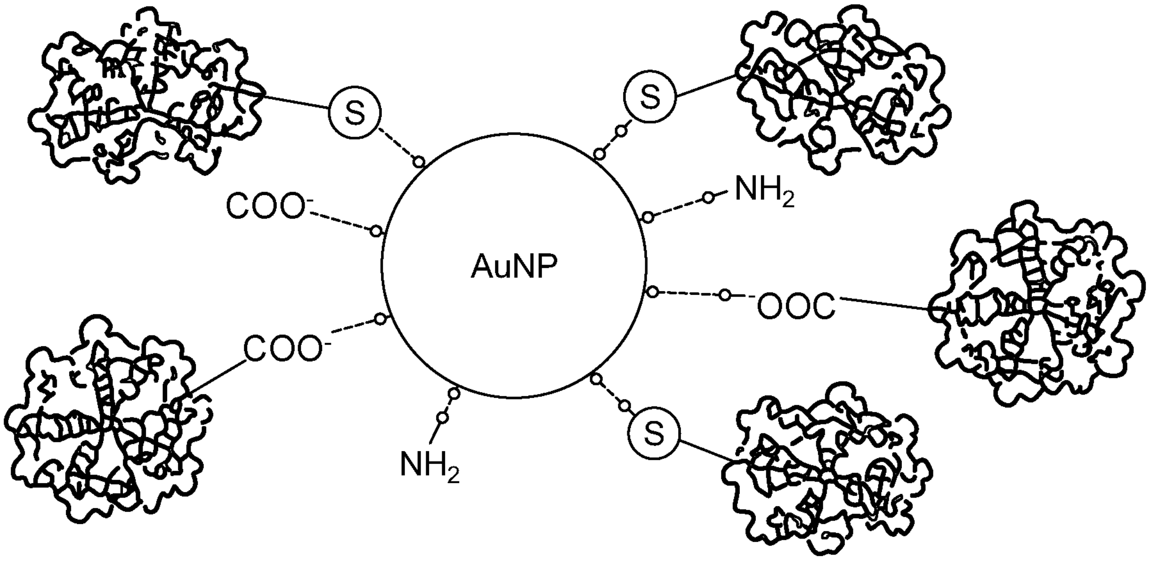
FIG. 3G illustrates coated gold nanoparticles using BSA, according to some embodiments.
Figure 3H:
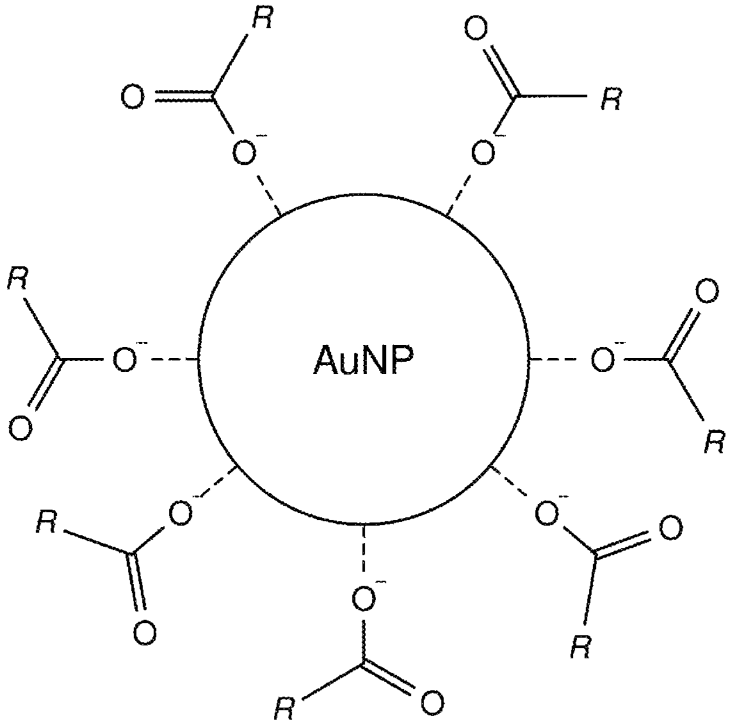
FIG. 3H illustrates coated gold nanoparticles using citrate, where the carboxylate groups adsorb onto the gold surface via electrostatic interaction, according to some embodiments.

| Capping Agent | Structure | Coating Schematic |
|---|---|---|
| Thiol-terminated Polyethylene Glycol (PEG) | $HS-[CH_2-CH_2-O]_n-CH_2-CH_2-OH$<br>n ≈ 10-100 | FIG. 3D |
| Polyvinyl-pyrrolidone (PVP) | 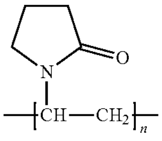 | FIG. 3E |
| BSA (Bovine Serum Albumin) | FIG. 3F | FIG. 3G |
| Citrate (CIT) (Citrate ion, $C_6H_5O_7^{3-}$) | 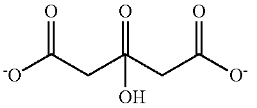 3Na$^+$ | FIG. 3H |

Figure 4A:
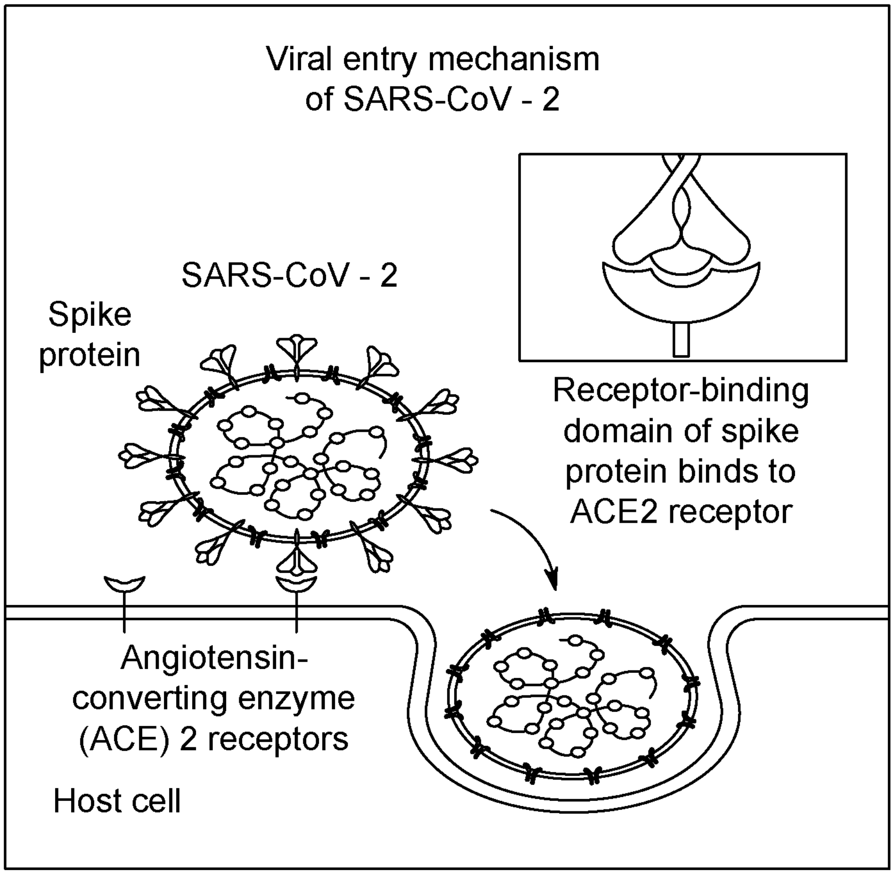
FIG. 4A illustrates a viral entry mechanism of SARS-CoV-2, according to some embodiments.

Example 3: Crystallization of Recombinant Human Furin Using the Modified Hanging Drop Method Since the emergence of the SARS-CoV-2 virus in 2019 (hereafter COVID-19), the resulting global pandemic has led to significant loss of life, damage to global economies and disruption to the way we all learn, work and live. The genetic sequencing of the COVID-19 virus was performed relatively quickly, leading to the development of new vaccines in record time. However, the development of new antiviral therapeutics for the virus took longer than anticipated. This is in part, related to the novelty of the virus and poor understanding of its mechanism of cell penetration. Studies have shown that angiotensin-converting enzyme II (ACE2) is important for the entry of the COVID-19 virus into host cells. The spike proteins on the virus are cleaved into subunits S1 and S2 during an infection (as shown in FIG. 4A). The S1 subunit is critical to the infection mechanism of the COVID-19 virus as it contains the receptor binding domain that binds ACE2 on the host cells. Since the proteolytic cleavage of the spike proteins is critical to the infectivity of SARS-CoV-2, therapeutics that hinder this initial step are effective in preventing COVID-19 infection.

Furins are $Ca^{2+}$ dependent serine end proteases that are found in human cells. Furin is a subtilisin-like proprotein convertase (PC) that cleaves at a specific cleavage motif present in the SARS-CoV-2 spike protein. Thus, the action of furin converts the inactive spike protein into smaller subunits that are implicated in infection. As a consequence of this, methods for the crystallization and characterization of furin crystal is critical for the development of new antiviral therapeutics that inhibit the action of this protein. Thus, the embodiments of the present disclosure describe a method with a focus on the furin protein because of its importance in SARS-CoV-2 infection. However, it is envisaged that the information gathered may also be used to support studies aimed at developing therapeutics for other related infections caused by coronaviruses. Since Furin is known to be abundant in the human body and given its role in activating substrates that are involved in a number of physiological processes, it is not straightforward to develop small molecule inhibitors of furin activity since this may inadvertently affect other important physiological processes in the body. This limits the number of therapeutic antiviral drugs that target the action of furin. The current state of the art in developing new furin inhibitors is to rely on a trial-and-error approach for the selection of the small molecule inhibitor, often based on Lipinski's rule of 5. Such an approach requires the effective re-crystallization of the protein-drug complex for further studies.

However, the conditions necessary for growing diffraction-quality crystals of furin-inhibitor complexes are not always obvious. This is, despite the fact that furin has been known since the 1980s and the fact that there are currently more than 20 crystal structures of furin in the protein data bank (PDB). The embodiments of the present disclosure describe a nanoparticle-induced protein crystallization (NIPC) method for the effective characterization of the crystal structures of furin and furin-inhibitor complexes for drug discovery applications. This will allow the development of new NIPC methods that will aid the discovery of new therapies against SARS-CoV-2 and other diseases where furin plays an important physiological role. The hypothesis tested is that furin crystallization can be aided by the presence of small quantities of nanoparticles.

Crystallization of Furin Using the Modified Hanging Drop Method

Figure 4B:
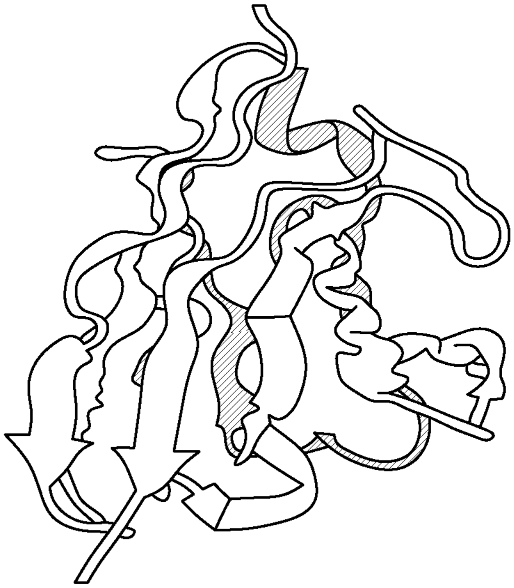
FIG. 4B illustrates the structure of recombinant human furin, according to some embodiments.
Figure 5:
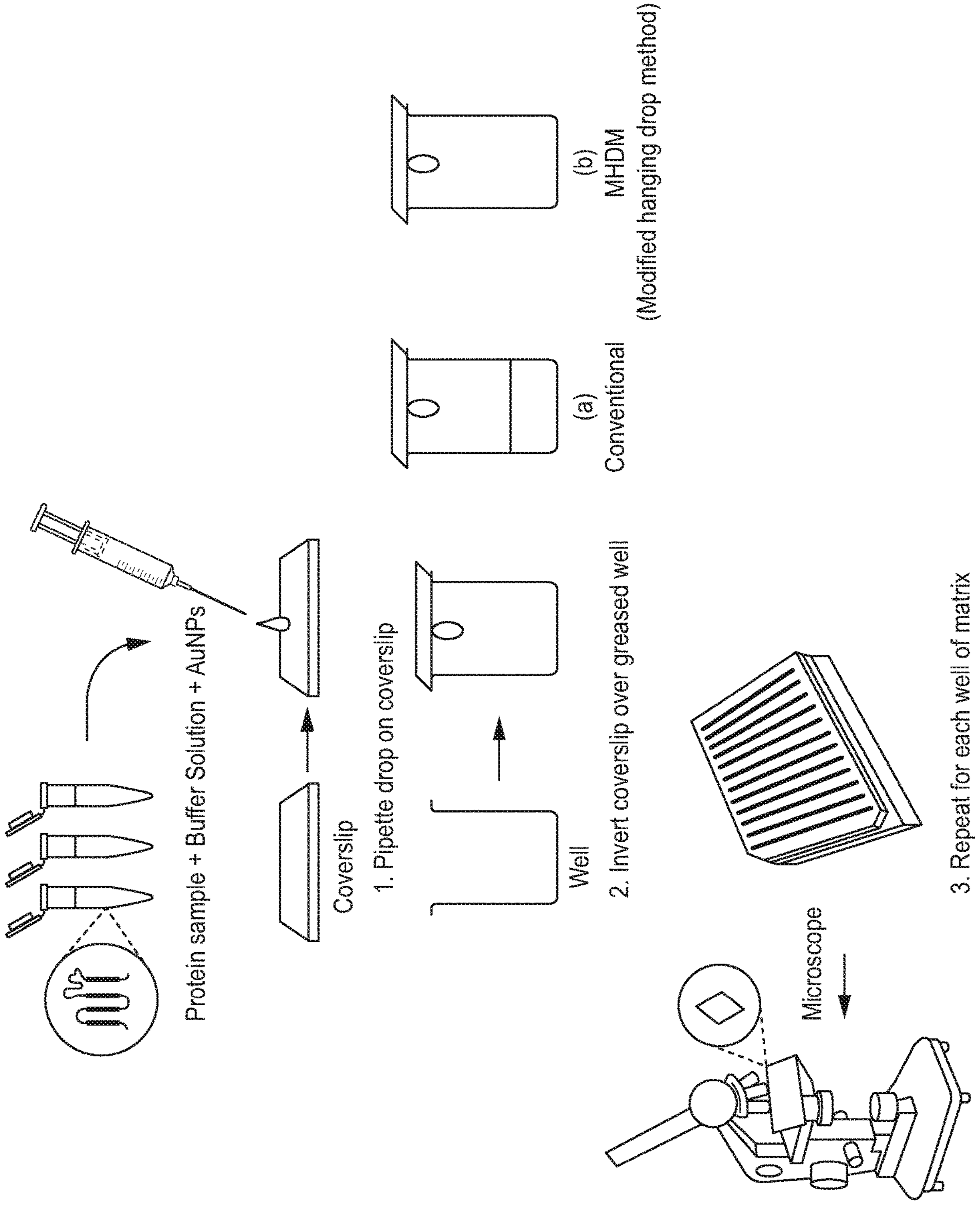
FIG. 5 is a schematic representation of the modified hanging drop method of protein crystallization.

The protocol involves taking equal amounts of protein solution and reagent drop in a 96-well Linbro plate. The protein sample should be homogenous, as pure as is practically possible (>95%), and free of amorphous material. Amorphous material is removed by centrifugation or microfiltration prior to use. The recommended sample protein concentration is 5-25 mg/ml in dilute (25 mM or less) buffer. Typically, a target protein solution of concentration of 9 mg/mL is used. The crystallization solution used in the prescreening protein crystallization kit includes the following reagents: 0.1 M tris, 0.1 M sodium potassium phosphate/2.8 M sodium chloride (pH 6.1-7)/20% (w/vol) and gold nanoparticles (AuNPs) coated with PEG4000. FIG. 4B illustrates the structure of recombinant human furin, according to some embodiments. The modified hanging drop method is used. FIG. 5 is a schematic representation of the modified hanging drop method of protein crystallization.

Recombinant human Furin was dissolved in 50 mM of buffer, pH 4.0, to a final concentration of 30 mg/ml$^{-1}$. Hanging drops were established with a total volume of 6 μl consisting of 3 μl buffer, 2 μl protein solution and 1 μl of NPs. Using a micropipette, a small drop (6 μL) of the protein solution was carefully dispensed onto the recess of the coverslip or glass slide. The coverslip was then inverted without disturbing the drop and placed onto the sealed well of the Linbro plate, followed by gently tapping down on the silicon grease on the rim of the Linbro plate to create an air-tight seal. This process was repeated with all the buffer combinations listed in the ultra-high condition, of at least 200 conditions. Once the matrix gets completed, the Linbro plate was positioned in an area of the laboratory, away from extreme vibrations, temperature fluctuations, and pedestrian traffic. The plate was allowed to rest undisturbed at a temperature of 18-22° C. or at room temperature to facilitate crystallization. To visually inspect the plate, the plate was inverted and placed on the stage of a standard laboratory microscope, ensuring that the coverslip is in focus. It is important to handle the drops with care to avoid disturbing the delicate crystallization process. Using this modified hanging drop method for the crystallization of furin, excellent quality crystals of furin were grown. The furin crystals were grown at room temperature.

Analysis of Protein Crystals Obtained by Using the Modified Hanging Drop Method

Single crystal X-ray was used to screen the protein crystals using a Rigaku Oxford Diffraction XtaLAB Synergy-S diffractometer equipped with a HyPix-6000HE Hybrid Photon Counting (HPC) detector with Cu microfocus sealed X-ray tube, as well as a low-temperature Oxford Cryosystems Cobra low temperature device (80K). The crystal screening strategy was calculated within CrysAlisPro PX mode (Rigaku OD, 2022) to ensure protein crystal screening strategy.

Figure 6A:
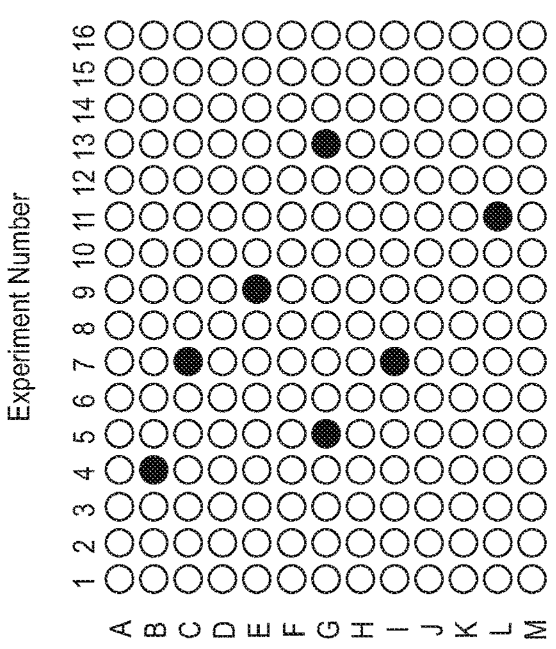
FIG. 6(A) and FIG. 6(B) show the Furin experimental data.
Figure 6B:
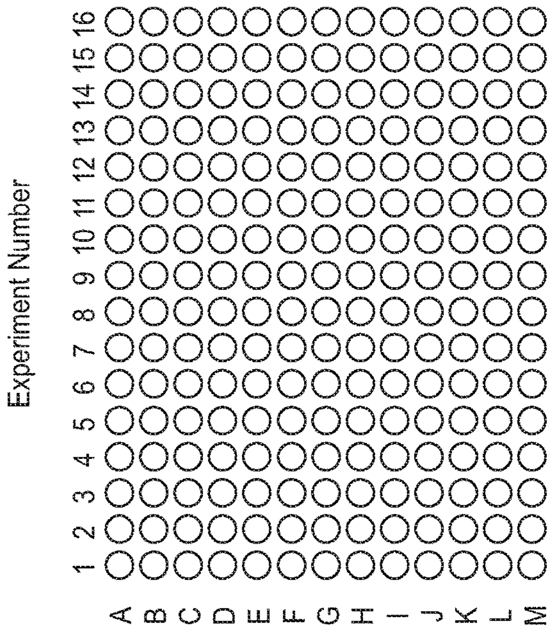
Figure 6C:
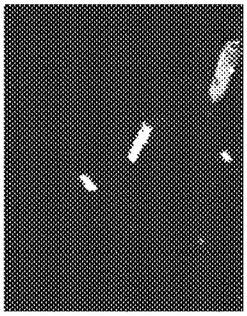
FIGS. 6(C)-6(G) show the Furin crystals at room temperature.
Figure 6D:
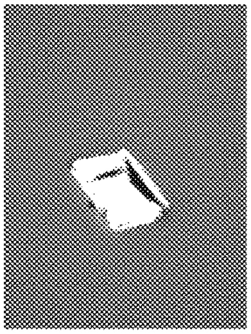
Figure 6E:
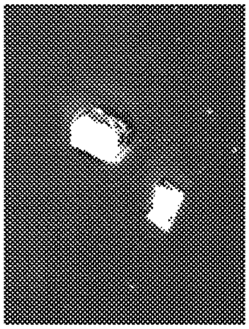
Figure 6F:
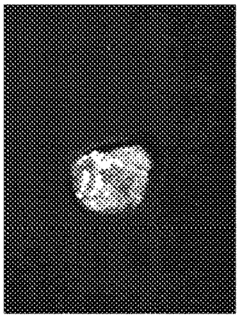
Figure 6G:
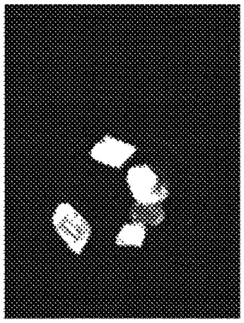

Protein crystal X-ray diffraction (XD) of furin is a technique used to determine the crystal structure of the furin protein. Understanding the crystal structure of furin can provide valuable insights into its biological function and help in the development of new drugs and therapies. To perform XRD analysis of furin crystals, the protein is first purified and crystallized using the techniques stated above. The crystals are then mounted on a thin fiber or loop and placed in the X-ray beam. The diffraction pattern is recorded using a detector, and the resulting data is analyzed using specialized software to determine the positions of the atoms in the crystal lattice. Recent studies have reported the crystal structure of furin in complex with various ligands, including small molecule inhibitors and substrate peptides. These structures have revealed key insights into the catalytic mechanism of furin and its interactions with other molecules. For example, the crystal structure of furin in complex with a small molecule inhibitor has shown that the inhibitor binds to the active site of the enzyme, blocking its activity. This information can be used to design new inhibitors with improved potency and selectivity. Overall, protein crystal XRD analysis of furin is an important tool for understanding the structure and function of this critical enzyme and for developing new treatments for diseases that involve Furin activity. FIG. 7B provides the crystal data of unit cell volume for Furin. TABLE 3 shows the Furins used for this study. Good quality crystals were obtained using the modified hanging drop method of protein crystallization. FIG. 6(C) and FIG. 6(G) show the Furin crystals at room temperature. FIG. 7A is a table showing the different protein conditions, buffers and nanoparticles used in the Furin experimental data of FIGS. 6(A)-6(G).

TABLE 3

| Furins used | | |
|---|---|---|
| 1 | Protein | Human Recombinant Furin |
| 2 | UnitProt Accession Number | P09958 |
| 3 | GenBank (refq) Accession number | 5045 |

While the disclosure has been described with reference to an exemplary embodiment(s), it will be understood by those skilled in the art that various changes may be made, and equivalents may be substituted for elements thereof without departing from the scope of the embodiment(s). In addition, many modifications may be made to adapt a particular situation or material to the teachings of the embodiment(s) without departing from the essential scope thereof. Therefore, it is intended that the disclosure is not limited to the disclosed embodiment(s), but that the disclosure will include all embodiments falling within the scope of the appended claims. Various examples have been described. These and other examples are within the scope of the following claims.

Other embodiments of the present disclosure are possible. Although the description above contains much specificity, these should not be construed as limiting the scope of the disclosure, but as merely providing illustrations of some of the presently preferred embodiments of this disclosure. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form various embodiments. Thus, it is intended that the scope of at least some of the present disclosure should not be limited by the particular disclosed embodiments described above.

Thus, the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

The foregoing description of various preferred embodiments of the disclosure have been presented for purposes of illustration and description. It is not intended to be exhaustive or to limit the disclosure to the precise embodiments, and obviously many modifications and variations are possible in light of the above teaching. The example embodiments, as described above, were chosen and described in order to best explain the principles of the disclosure and its practical application to thereby enable others skilled in the art to best utilize the disclosure in various embodiments and with various modifications as are suited to the particular use contemplated. It is intended that the scope of the disclosure be defined by the claims appended hereto.

Various examples have been described. These and other examples are within the scope of the following claims.

TABLE 4

Ultra-high Protein Conditions for Prescreening of Protein Crystallization

| Reagent | Units | Salt | Gold Nanoparticles + PEG 4000 | PEG |
|---|---|---|---|---|
| 1 | 0.1M | Ammonium acetate | AuNP + Polyethylene glycol 4000 | 4% v/v |
| 2 | 0.4M | Ammonium acetate | AuNP + Polyethylene glycol 4000 | 6% v/v |
| 3 | 0.6M | Ammonium acetate | AuNP + Polyethylene glycol 4000 | 8% v/v |
| 4 | 0.8M | Ammonium acetate | AuNP + Polyethylene glycol 4000 | 10% v/v |
| 5 | 1.0M | Ammonium acetate | AuNP + Polyethylene glycol 4000 | 14% v/v |
| 6 | 1.4M | Ammonium acetate | AuNP + Polyethylene glycol 4000 | 16% v/v |
| 7 | 0.1M | Potassium acetate | AuNP + Polyethylene glycol 4000 | 4% v/v |
| 8 | 0.4M | Potassium acetate | AuNP + Polyethylene glycol 4000 | 6% v/v |
| 9 | 0.6M | Potassium acetate | AuNP + Polyethylene glycol 4000 | 8% v/v |
| 10 | 0.8M | Potassium acetate | AuNP + Polyethylene glycol 4000 | 10% v/v |
| 11 | 1.0M | Potassium acetate | AuNP + Polyethylene glycol 4000 | 14% v/v |
| 12 | 1.4M | Potassium acetate | AuNP + Polyethylene glycol 4000 | 16% v/v |
| 13 | 0.1M | Sodium Chloride | AuNP + Polyethylene glycol 4000 | 4% v/v |
| 14 | 0.4M | Sodium Chloride | AuNP + Polyethylene glycol 4000 | 6% v/v |
| 15 | 0.6M | Sodium Chloride | AuNP + Polyethylene glycol 4000 | 8% v/v |
| 16 | 0.8M | Sodium Chloride | AuNP + Polyethylene glycol 4000 | 10% v/v |
| 17 | 1.0M | Sodium Chloride | AuNP + Polyethylene glycol 4000 | 14% v/v |
| 18 | 1.4M | Sodium Chloride | AuNP + Polyethylene glycol 4000 | 16% v/v |
| 19 | 0.1M | Ammonium formate | AuNP + Polyethylene glycol 4000 | 4% v/v |
| 20 | 0.4M | Ammonium formate | AuNP + Polyethylene glycol 4000 | 6% v/v |
| 21 | 0.6M | Ammonium formate | AuNP + Polyethylene glycol 4000 | 8% v/v |
| 22 | 0.8M | Ammonium formate | AuNP + Polyethylene glycol 4000 | 10% v/v |
| 23 | 1.0M | Ammonium formate | AuNP + Polyethylene glycol 4000 | 14% v/v |
| 24 | 1.4M | Ammonium formate | AuNP + Polyethylene glycol 4000 | 16% v/v |
| 25 | 0.1M | Succinic acid pH 7.0 | AuNP + Polyethylene glycol 4000 | 4% v/v |
| 26 | 0.4M | Succinic acid pH 7.1 | AuNP + Polyethylene glycol 4000 | 6% v/v |
| 27 | 0.6M | Succinic acid pH 7.2 | AuNP + Polyethylene glycol 4000 | 8% v/v |
| 28 | 0.8M | Succinic acid pH 7.3 | AuNP + Polyethylene glycol 4000 | 10% v/v |
| 29 | 1.0M | Succinic acid pH 7.4 | AuNP + Polyethylene glycol 4000 | 14% v/v |
| 30 | 1.4M | Succinic acid pH 7.5 | AuNP + Polyethylene glycol 4000 | 16% v/v |
| 31 | 0.1M | Potassium sodium tartrate tetrahydrate | AuNP + Polyethylene glycol 4000 | 4% v/v |
| 32 | 0.4M | Potassium sodium tartrate tetrahydrate | AuNP + Polyethylene glycol 4000 | 6% v/v |
| 33 | 0.6M | Potassium sodium tartrate tetrahydrate | AuNP + Polyethylene glycol 4000 | 8% v/v |
| 34 | 0.8M | Potassium sodium tartrate tetrahydrate | AuNP + Polyethylene glycol 4000 | 10% v/v |
| 35 | 1.0M | Potassium sodium tartrate tetrahydrate | AuNP + Polyethylene glycol 4000 | 14% v/v |
| 36 | 1.4M | Potassium sodium tartrate tetrahydrate | AuNP + Polyethylene glycol 4000 | 16% v/v |
| 37 | 0.1M | Potassium thiocyanate | AuNP + Polyethylene glycol 4000 | 4% v/v |
| 38 | 0.4M | Potassium thiocyanate | AuNP + Polyethylene glycol 4000 | 6% v/v |
| 39 | 0.6M | Potassium thiocyanate | AuNP + Polyethylene glycol 4000 | 8% v/v |
| 40 | 0.8M | Potassium thiocyanate | AuNP + Polyethylene glycol 4000 | 10% v/v |
| 41 | 1.0M | Potassium thiocyanate | AuNP + Polyethylene glycol 4000 | 14% v/v |
| 42 | 1.4M | Potassium thiocyanate | AuNP + Polyethylene glycol 4000 | 16% v/v |
| 43 | 0.1M | Tacsimate pH 7.0 | AuNP + Polyethylene glycol 4000 | 4% v/v |
| 44 | 0.4M | Tacsimate pH 7.1 | AuNP + Polyethylene glycol 4000 | 6% v/v |
| 45 | 0.6M | Tacsimate pH 7.2 | AuNP + Polyethylene glycol 4000 | 8% v/v |
| 46 | 0.8M | Tacsimate pH 7.3 | AuNP + Polyethylene glycol 4000 | 10% v/v |
| 47 | 1.0M | Tacsimate pH 7.4 | AuNP + Polyethylene glycol 4000 | 14% v/v |
| 48 | 1.4M | Tacsimate pH 7.5 | AuNP + Polyethylene glycol 4000 | 16% v/v |
| 49 | 0.1M | Magnesium sulfate hydrate | AuNP + Polyethylene glycol 4000 | 4% v/v |
| 50 | 0.4M | Magnesium sulfate hydrate | AuNP + Polyethylene glycol 4000 | 6% v/v |
| 51 | 0.6M | Magnesium sulfate hydrate | AuNP + Polyethylene glycol 4000 | 8% v/v |
| 52 | 0.8M | Magnesium sulfate hydrate | AuNP + Polyethylene glycol 4000 | 10% v/v |
| 53 | 1.0M | Magnesium sulfate hydrate | AuNP + Polyethylene glycol 4000 | 14% v/v |
| 54 | 1.4M | Magnesium sulfate hydrate | AuNP + Polyethylene glycol 4000 | 16% v/v |
| 55 | 0.1M | Lithium sulfate monohydrate | AuNP + Polyethylene glycol 4000 | 4% v/v |
| 56 | 0.4M | Lithium sulfate monohydrate | AuNP + Polyethylene glycol 4000 | 6% v/v |
| 57 | 0.6M | Lithium sulfate monohydrate | AuNP + Polyethylene glycol 4000 | 8% v/v |
| 58 | 0.8M | Lithium sulfate monohydrate | AuNP + Polyethylene glycol 4000 | 10% v/v |
| 59 | 1.0M | Lithium sulfate monohydrate | AuNP + Polyethylene glycol 4000 | 14% v/v |
| 60 | 1.4M | Lithium sulfate monohydrate | AuNP + Polyethylene glycol 4000 | 16% v/v |
| 61 | 0.1M | Ammonium tartrate dibasic | AuNP + Polyethylene glycol 4000 | 4% v/v |
| 62 | 0.4M | Ammonium tartrate dibasic | AuNP + Polyethylene glycol 4000 | 6% v/v |
| 63 | 0.6M | Ammonium tartrate dibasic | AuNP + Polyethylene glycol 4000 | 8% v/v |
| 64 | 0.8M | Ammonium tartrate dibasic | AuNP + Polyethylene glycol 4000 | 10% v/v |
| 65 | 1.0M | Ammonium tartrate dibasic | AuNP + Polyethylene glycol 4000 | 14% v/v |
| 66 | 1.4M | Ammonium tartrate dibasic | AuNP + Polyethylene glycol 4000 | 16% v/v |
| 67 | 0.1M | Sodium formate | AuNP + Polyethylene glycol 4000 | 4% v/v |
| 68 | 0.4M | Sodium formate | AuNP + Polyethylene glycol 4000 | 6% v/v |
| 69 | 0.6M | Sodium formate | AuNP + Polyethylene glycol 4000 | 8% v/v |
| 70 | 0.8M | Sodium formate | AuNP + Polyethylene glycol 4000 | 10% v/v |
| 71 | 1.0M | Sodium formate | AuNP + Polyethylene glycol 4000 | 14% v/v |
| 72 | 1.4M | Sodium formate | AuNP + Polyethylene glycol 4000 | 16% v/v |
| 73 | 0.1M | DL-Malic acid pH 7.0 | AuNP + Polyethylene glycol 4000 | 4% v/v |
| 74 | 0.4M | DL-Malic acid pH 7.1 | AuNP + Polyethylene glycol 4000 | 6% v/v |
| 75 | 0.6M | DL-Malic acid pH 7.2 | AuNP + Polyethylene glycol 4000 | 8% v/v |
| 76 | 0.8M | DL-Malic acid pH 7.3 | AuNP + Polyethylene glycol 4000 | 10% v/v |

TABLE 4-continued

Ultra-high Protein Conditions for Prescreening of Protein Crystallization

| Reagent | Units | Salt | Gold Nanoparticles + PEG 4000 | PEG |
|---|---|---|---|---|
| 77 | 1.0M | DL-Malic acid pH 7.4 | AuNP + Polyethylene glycol 4000 | 14% v/v |
| 78 | 1.4M | DL-Malic acid pH 7.5 | AuNP + Polyethylene glycol 4000 | 16% v/v |
| 79 | 0.1M | Magnesium formate dihydrate | AuNP + Polyethylene glycol 4000 | 4% v/v |
| 80 | 0.4M | Magnesium formate dihydrate | AuNP + Polyethylene glycol 4000 | 6% v/v |
| 81 | 0.6M | Magnesium formate dihydrate | AuNP + Polyethylene glycol 4000 | 8% v/v |
| 82 | 0.8M | Magnesium formate dihydrate | AuNP + Polyethylene glycol 4000 | 10% v/v |
| 83 | 1.0M | Magnesium formate dihydrate | AuNP + Polyethylene glycol 4000 | 14% v/v |
| 84 | 1.4M | Magnesium formate dihydrate | AuNP + Polyethylene glycol 4000 | 16% v/v |
| 85 | 0.1M | Sodium malonate pH 7.0 | AuNP + Polyethylene glycol 4000 | 4% v/v |
| 86 | 0.4M | Sodium malonate pH 7.1 | AuNP + Polyethylene glycol 4000 | 6% v/v |
| 87 | 0.6M | Sodium malonate pH 7.2 | AuNP + Polyethylene glycol 4000 | 8% v/v |
| 88 | 0.8M | Sodium malonate pH 7.3 | AuNP + Polyethylene glycol 4000 | 10% v/v |
| 89 | 1.0M | Sodium malonate pH 7.4 | AuNP + Polyethylene glycol 4000 | 14% v/v |
| 90 | 1.4M | Sodium malonate pH 7.5 | AuNP + Polyethylene glycol 4000 | 16% v/v |
| 91 | 0.1M | Ammonium nitrate | AuNP + Polyethylene glycol 4000 | 4% v/v |
| 92 | 0.4M | Ammonium nitrate | AuNP + Polyethylene glycol 4000 | 6% v/v |
| 94 | 0.6M | Ammonium nitrate | AuNP + Polyethylene glycol 4000 | 8% v/v |
| 95 | 0.8M | Ammonium nitrate | AuNP + Polyethylene glycol 4000 | 10% v/v |
| 96 | 1.0M | Ammonium nitrate | AuNP + Polyethylene glycol 4000 | 14% v/v |
| 97 | 1.4M | Ammonium nitrate | AuNP + Polyethylene glycol 4000 | 16% v/v |
| 98 | 0.1M | Ethylammonium nitrate | AuNP + Polyethylene glycol 4000 | 4% v/v |
| 99 | 0.4M | Ethylammonium nitrate | AuNP + Polyethylene glycol 4000 | 6% v/v |
| 100 | 0.6M | Ethylammonium nitrate | AuNP + Polyethylene glycol 4000 | 8% v/v |
| 101 | 0.8M | Ethylammonium nitrate | AuNP + Polyethylene glycol 4000 | 10% v/v |
| 102 | 1.0M | Ethylammonium nitrate | AuNP + Polyethylene glycol 4000 | 14% v/v |
| 103 | 1.4M | Ethylammonium nitrate | AuNP + Polyethylene glycol 4000 | 16% v/v |
| 104 | 0.1M | Magnesium nitrate hexahydrate | AuNP + Polyethylene glycol 4000 | 4% v/v |
| 105 | 0.4M | Magnesium nitrate hexahydrate | AuNP + Polyethylene glycol 4000 | 6% v/v |
| 106 | 0.6M | Magnesium nitrate hexahydrate | AuNP + Polyethylene glycol 4000 | 8% v/v |
| 107 | 0.8M | Magnesium nitrate hexahydrate | AuNP + Polyethylene glycol 4000 | 10% v/v |
| 108 | 1.0M | Magnesium nitrate hexahydrate | AuNP + Polyethylene glycol 4000 | 14% v/v |
| 109 | 1.4M | Magnesium nitrate hexahydrate | AuNP + Polyethylene glycol 4000 | 16% v/v |
| 110 | 0.1M | Sodium nitrate | AuNP + Polyethylene glycol 4000 | 4% v/v |
| 111 | 0.4M | Sodium nitrate | AuNP + Polyethylene glycol 4000 | 6% v/v |
| 112 | 0.6M | Sodium nitrate | AuNP + Polyethylene glycol 4000 | 8% v/v |
| 113 | 0.8M | Sodium nitrate | AuNP + Polyethylene glycol 4000 | 10% v/v |
| 114 | 1.0M | Sodium nitrate | AuNP + Polyethylene glycol 4000 | 14% v/v |
| 115 | 1.4M | Sodium nitrate | AuNP + Polyethylene glycol 4000 | 16% v/v |
| 116 | 0.1M | Potassium phosphate dibasic | AuNP + Polyethylene glycol 4000 | 4% v/v |
| 117 | 0.4M | Potassium phosphate dibasic | AuNP + Polyethylene glycol 4000 | 6% v/v |
| 118 | 0.6M | Potassium phosphate dibasic | AuNP + Polyethylene glycol 4000 | 8% v/v |
| 119 | 0.8M | Potassium phosphate dibasic | AuNP + Polyethylene glycol 4000 | 10% v/v |
| 120 | 1.0M | Potassium phosphate dibasic | AuNP + Polyethylene glycol 4000 | 14% v/v |
| 121 | 1.4M | Potassium phosphate dibasic | AuNP + Polyethylene glycol 4000 | 16% v/v |
| 122 | 0.1M | Sodium/Potassium phosphate pH 7.0 | AuNP + Polyethylene glycol 4000 | 4% v/v |
| 123 | 0.4M | Sodium/Potassium phosphate pH 7.1 | AuNP + Polyethylene glycol 4000 | 6% v/v |
| 124 | 0.6M | Sodium/Potassium phosphate pH 7.2 | AuNP + Polyethylene glycol 4000 | 8% v/v |
| 125 | 0.8M | Sodium/Potassium phosphate pH 7.3 | AuNP + Polyethylene glycol 4000 | 10% v/v |
| 126 | 1.0M | Sodium/Potassium phosphate pH 7.4 | AuNP + Polyethylene glycol 4000 | 14% v/v |
| 127 | 1.4M | Sodium/Potassium phosphate pH 7.5 | AuNP + Polyethylene glycol 4000 | 16% v/v |
| 128 | 0.1M | Sodium thiocyanate | AuNP + Polyethylene glycol 4000 | 4% v/v |
| 129 | 0.4M | Sodium thiocyanate | AuNP + Polyethylene glycol 4000 | 6% v/v |
| 130 | 0.6M | Sodium thiocyanate | AuNP + Polyethylene glycol 4000 | 8% v/v |
| 131 | 0.8M | Sodium thiocyanate | AuNP + Polyethylene glycol 4000 | 10% v/v |
| 132 | 1.0M | Sodium thiocyanate | AuNP + Polyethylene glycol 4000 | 14% v/v |
| 133 | 1.4M | Sodium thiocyanate | AuNP + Polyethylene glycol 4000 | 16% v/v |
| 134 | 0.1M | Sodium tartrate dibasic dihydrate | AuNP + Polyethylene glycol 4000 | 4% v/v |
| 135 | 0.4M | Sodium tartrate dibasic dihydrate | AuNP + Polyethylene glycol 4000 | 6% v/v |
| 136 | 0.6M | Sodium tartrate dibasic dihydrate | AuNP + Polyethylene glycol 4000 | 8% v/v |
| 137 | 0.8M | Sodium tartrate dibasic dihydrate | AuNP + Polyethylene glycol 4000 | 10% v/v |
| 138 | 1.0M | Sodium tartrate dibasic dihydrate | AuNP + Polyethylene glycol 4000 | 14% v/v |
| 139 | 1.4M | Sodium tartrate dibasic dihydrate | AuNP + Polyethylene glycol 4000 | 16% v/v |
| 140 | 0.1M | Ammonium phosphate dibasic | AuNP + Polyethylene glycol 4000 | 4% v/v |
| 141 | 0.4M | Ammonium phosphate dibasic | AuNP + Polyethylene glycol 4000 | 6% v/v |
| 142 | 0.6M | Ammonium phosphate dibasic | AuNP + Polyethylene glycol 4000 | 8% v/v |
| 143 | 0.8M | Ammonium phosphate dibasic | AuNP + Polyethylene glycol 4000 | 10% v/v |
| 144 | 1.0M | Ammonium phosphate dibasic | AuNP + Polyethylene glycol 4000 | 14% v/v |
| 145 | 1.4M | Ammonium phosphate dibasic | AuNP + Polyethylene glycol 4000 | 16% v/v |
| 146 | 0.1M | Lithium nitrate | AuNP + Polyethylene glycol 4000 | 4% v/v |
| 147 | 0.4M | Lithium nitrate | AuNP + Polyethylene glycol 4000 | 6% v/v |
| 148 | 0.6M | Lithium nitrate | AuNP + Polyethylene glycol 4000 | 8% v/v |
| 149 | 0.8M | Lithium nitrate | AuNP + Polyethylene glycol 4000 | 10% v/v |
| 150 | 1.0M | Lithium nitrate | AuNP + Polyethylene glycol 4000 | 14% v/v |
| 151 | 1.4M | Lithium nitrate | AuNP + Polyethylene glycol 4000 | 16% v/v |
| 152 | 0.1M | Ammonium citrate dibasic | AuNP + Polyethylene glycol 4000 | 4% v/v |
| 153 | 0.4M | Ammonium citrate dibasic | AuNP + Polyethylene glycol 4000 | 6% v/v |

TABLE 4-continued

Ultra-high Protein Conditions for Prescreening of Protein Crystallization

| Reagent | Units | Salt | Gold Nanoparticles + PEG 4000 | PEG |
|---|---|---|---|---|
| 154 | 0.6M | Ammonium citrate dibasic | AuNP + Polyethylene glycol 4000 | 8% v/v |
| 155 | 0.8M | Ammonium citrate dibasic | AuNP + Polyethylene glycol 4000 | 10% v/v |
| 156 | 1.0M | Ammonium citrate dibasic | AuNP + Polyethylene glycol 4000 | 14% v/v |
| 157 | 1.4M | Ammonium citrate dibasic | AuNP + Polyethylene glycol 4000 | 16% v/v |
| 158 | 0.1M | Ammonium chloride | AuNP + Polyethylene glycol 4000 | 4% v/v |
| 159 | 0.4M | Ammonium chloride | AuNP + Polyethylene glycol 4000 | 6% v/v |
| 160 | 0.6M | Ammonium chloride | AuNP + Polyethylene glycol 4000 | 8% v/v |
| 161 | 0.8M | Ammonium chloride | AuNP + Polyethylene glycol 4000 | 10% v/v |
| 162 | 1.0M | Ammonium chloride | AuNP + Polyethylene glycol 4000 | 14% v/v |
| 163 | 1.4M | Ammonium chloride | AuNP + Polyethylene glycol 4000 | 16% v/v |
| 164 | 0.1M | Lithium citrate tribasic tetrahydrate | AuNP + Polyethylene glycol 4000 | 4% v/v |
| 165 | 0.4M | Lithium citrate tribasic tetrahydrate | AuNP + Polyethylene glycol 4000 | 6% v/v |
| 166 | 0.6M | Lithium citrate tribasic tetrahydrate | AuNP + Polyethylene glycol 4000 | 8% v/v |
| 167 | 0.8M | Lithium citrate tribasic tetrahydrate | AuNP + Polyethylene glycol 4000 | 10% v/v |
| 168 | 1.0M | Lithium citrate tribasic tetrahydrate | AuNP + Polyethylene glycol 4000 | 14% v/v |
| 169 | 1.4M | Lithium citrate tribasic tetrahydrate | AuNP + Polyethylene glycol 4000 | 16% v/v |
| 170 | 0.1M | Ammonium citrate tribasic pH 7.0 | AuNP + Polyethylene glycol 4000 | 4% v/v |
| 171 | 0.4M | Ammonium citrate tribasic pH 7.1 | AuNP + Polyethylene glycol 4000 | 6% v/v |
| 172 | 0.6M | Ammonium citrate tribasic pH 7.2 | AuNP + Polyethylene glycol 4000 | 8% v/v |
| 173 | 0.8M | Ammonium citrate tribasic pH 7.3 | AuNP + Polyethylene glycol 4000 | 10% v/v |
| 174 | 1.0M | Ammonium citrate tribasic pH 7.4 | AuNP + Polyethylene glycol 4000 | 14% v/v |
| 175 | 1.4M | Ammonium citrate tribasic pH 7.5 | AuNP + Polyethylene glycol 4000 | 16% v/v |
| 176 | 0.1M | Lithium chloride | AuNP + Polyethylene glycol 4000 | 4% v/v |
| 177 | 0.4M | Lithium chloride | AuNP + Polyethylene glycol 4000 | 6% v/v |
| 178 | 0.6M | Lithium chloride | AuNP + Polyethylene glycol 4000 | 8% v/v |
| 179 | 0.8M | Lithium chloride | AuNP + Polyethylene glycol 4000 | 10% v/v |
| 180 | 1.0M | Lithium chloride | AuNP + Polyethylene glycol 4000 | 14% v/v |
| 181 | 1.4M | Lithium chloride | AuNP + Polyethylene glycol 4000 | 16% v/v |
| 182 | 0.1M | Zinc acetate dihydrate | AuNP + Polyethylene glycol 4000 | 4% v/v |
| 183 | 0.4M | Zinc acetate dihydrate | AuNP + Polyethylene glycol 4000 | 6% v/v |
| 184 | 0.6M | Zinc acetate dihydrate | AuNP + Polyethylene glycol 4000 | 8% v/v |
| 185 | 0.8M | Zinc acetate dihydrate | AuNP + Polyethylene glycol 4000 | 10% v/v |
| 186 | 1.0M | Zinc acetate dihydrate | AuNP + Polyethylene glycol 4000 | 14% v/v |
| 187 | 1.4M | Zinc acetate dihydrate | AuNP + Polyethylene glycol 4000 | 16% v/v |
| 188 | 0.1M | Nickel (II) chloride hexahydrate | AuNP + Polyethylene glycol 4000 | 4% v/v |
| 189 | 0.4M | Nickel (II) chloride hexahydrate | AuNP + Polyethylene glycol 4000 | 6% v/v |
| 190 | 0.6M | Nickel (II) chloride hexahydrate | AuNP + Polyethylene glycol 4000 | 8% v/v |
| 191 | 0.8M | Nickel(II) chloride hexahydrate | AuNP + Polyethylene glycol 4000 | 10% v/v |
| 192 | 1.0M | Nickel (II) chloride hexahydrate | AuNP + Polyethylene glycol 4000 | 14% v/v |
| 193 | 1.4M | Nickel (II) chloride hexahydrate | AuNP + Polyethylene glycol 4000 | 16% v/v |
| 194 | 0.1M | Cadmium chloride hydrate | AuNP + Polyethylene glycol 4000 | 4% v/v |
| 195 | 0.4M | Cadmium chloride hydrate | AuNP + Polyethylene glycol 4000 | 6% v/v |
| 196 | 0.6M | Cadmium chloride hydrate | AuNP + Polyethylene glycol 4000 | 8% v/v |
| 197 | 0.8M | Cadmium chloride hydrate | AuNP + Polyethylene glycol 4000 | 10% v/v |
| 198 | 1.0M | Cadmium chloride hydrate | AuNP + Polyethylene glycol 4000 | 14% v/v |
| 199 | 1.4M | Cadmium chloride hydrate | AuNP + Polyethylene glycol 4000 | 16% v/v |
| 200 | 0.1M | Potassium citrate tribasic monohydrate | AuNP + Polyethylene glycol 4000 | 4% v/v |
| 201 | 0.4M | Potassium citrate tribasic monohydrate | AuNP + Polyethylene glycol 4000 | 6% v/v |
| 202 | 0.6M | Potassium citrate tribasic monohydrate | AuNP + Polyethylene glycol 4000 | 8% v/v |
| 203 | 0.8M | Potassium citrate tribasic monohydrate | AuNP + Polyethylene glycol 4000 | 10% v/v |
| 204 | 1.0M | Potassium citrate tribasic monohydrate | AuNP + Polyethylene glycol 4000 | 14% v/v |
| 205 | 1.4M | Potassium citrate tribasic monohydrate | AuNP + Polyethylene glycol 4000 | 16% v/v |
| 206 | 0.1M | Sodium acetate trihydrate | AuNP + Polyethylene glycol 4000 | 4% v/v |
| 207 | 0.4M | Sodium acetate trihydrate | AuNP + Polyethylene glycol 4000 | 6% v/v |
| 208 | 0.6M | Sodium acetate trihydrate | AuNP + Polyethylene glycol 4000 | 8% v/v |
| 209 | 0.8M | Sodium acetate trihydrate | AuNP + Polyethylene glycol 4000 | 10% v/v |
| 210 | 1.0M | Sodium acetate trihydrate | AuNP + Polyethylene glycol 4000 | 14% v/v |
| 211 | 1.4M | Sodium acetate trihydrate | AuNP + Polyethylene glycol 4000 | 16% v/v |
| 212 | 0.1M | Tris | AuNP + Polyethylene glycol 4000 | 4% v/v |
| 213 | 0.4M | Tris | AuNP + Polyethylene glycol 4000 | 6% v/v |
| 214 | 0.6M | Tris | AuNP + Polyethylene glycol 4000 | 8% v/v |
| 215 | 0.8M | Tris | AuNP + Polyethylene glycol 4000 | 10% v/v |
| 216 | 1.0M | Tris | AuNP + Polyethylene glycol 4000 | 14% v/v |
| 217 | 1.4M | Tris | AuNP + Polyethylene glycol 4000 | 16% v/v |

What is claimed is:

1. An ultra-high condition prescreening protein crystallization kit, comprising:

(a) gold nanoparticles coated with PEG (polyethylene glycol), wherein the polyethylene glycol (PEG) is covalently attached to the gold nanoparticles via a thiol functional group, and wherein the gold nanoparticles exhibit an average particle diameter ranging from 2 nm to 52 nm;

(b) ultra-high conditions scaled up to screen, wherein the ultra-high conditions include a plurality of buffer conditions;

(c) a plurality of coverslips with a recess; and (d) a plurality of greased reservoirs;

wherein the ultra-high condition prescreening protein crystallization kit uses a modified hanging drop method for carrying out protein crystallization.

2. The ultra-high condition kit of claim 1, wherein at least 96 conditions are scaled up to screen.

3. The ultra-high condition kit of claim 1, wherein the recess has a capacity in a range of 0.2 μl-20 μl.

4. The ultra-high condition kit of claim 1, wherein the gold nanoparticles are coated with PEG in different concentrations of buffer.

5. The ultra-high condition kit of claim 1, wherein the gold nanoparticles are monodispersed with the average particle diameter of the gold nanoparticles ranging from 10.0 nm to 20.0 nm.

6. The ultra-high condition kit of claim 1, wherein the gold nanoparticles are stable at room temperature with a shelf life of 3-5 years.

7. A modified hanging drop method for protein crystallization, comprising:

(a) providing a coverslip having a recess;

(b) pouring a target protein solution and a precipitant solution in the recess sufficient to form a drop; wherein the precipitant solution includes gold nanoparticles;

(c) inverting the coverslip without disturbing the drop;

(d) placing the inverted coverslip onto a greased reservoir, wherein a rim of the greased reservoir is greased;

(e) applying pressure on the grease to create an airtight seal;

(f) repeating steps (a) to (e) with all buffer combinations listed in ultra-high conditions;

(g) allowing the coverslip to rest undisturbed at a temperature of 18-22° C. to facilitate crystallization; and (h) visually inspecting the coverslip for crystallization.

8. The method of claim 7, wherein the greased reservoir further comprises the precipitant solution.

9. The method of claim 7, wherein the coverslip is a silanated plastic coverslip.

10. The method of claim 7, wherein the recess has a capacity in a range of 0.2 μl-20 μl.

11. The method of claim 7, wherein the target protein solution comprises the protein to be crystallized, with the target protein in a concentration of 5 mg/ml to 40 mg/ml.

12. The method of claim 7, wherein the target protein is in a buffer solution; the buffer solution comprising one or more of the buffers given in the ultra-high conditions.

13. The method of claim 7, wherein the precipitant solution comprises the gold nanoparticles in a buffer.

14. The method of claim 13, wherein the gold nanoparticles are coated with one or more capping agents; the one or more capping agents comprising one or more of PEG, PVP, BSA, CIT.

15. The method of claim 7, wherein the gold nanoparticles are monodispersed with an average particle diameter of the nanoparticles ranging from 10.0 nm to 20.0 nm.

16. The method of claim 7, wherein a duration of crystallization ranges from 2 hours to 245 hours.

17. A method for protein crystallization, comprising:

adding a mixture to a substrate in the form of a drop, wherein the mixture includes a nucleation-inducing reagent, one or more buffers, and a target protein, wherein the nucleation-inducing reagent includes gold nanoparticles coated with polyethylene glycol (PEG), wherein the polyethylene glycol (PEG) is covalently attached to the gold nanoparticles via a thiol functional group, and wherein the gold nanoparticles exhibit an average particle diameter ranging from 2.5 nm to 10 nm;

orienting the substrate to suspend the drop over a reservoir; and inducing vapor diffusion using crystallization conditions for an exposure time sufficient to form a protein-containing crystal, wherein the nucleation-inducing reagent promotes nucleation.

18. The method of claim 17, wherein the substrate is a silanated coverslip including a recess.

19. The method of claim 17, wherein the average particle diameter of the gold nanoparticles ranges from 3 nm to 6 nm, and wherein the mixture is formed using a solution including the target protein, wherein a concentration of the target protein in the solution ranges from 5 mg/ml to 40 mg/ml.

20. The method of claim 17, wherein orienting the substrate to suspend the drop over the reservoir includes forming an airtight seal, wherein crystallization conditions include exposing the drop to a temperature ranging from 15° C. to 30° C., and wherein the exposure time ranges from 3 hours to 14 hours.

* * * * *